United States Patent [19]

Buzby, Jr. et al.

[11] Patent Number: 5,144,072
[45] Date of Patent: * Sep. 1, 1992

[54] ANTI-ARRHYTHMIC AGENTS

[75] Inventors: George C. Buzby, Jr., Blue Bell; Thomas J. Colatsky, Devon, both of Pa.

[73] Assignee: American Home Products Corporation, New York, N.Y.

[*] Notice: The portion of the term of this patent subsequent to Jan. 26, 2005 has been disclaimed.

[21] Appl. No.: 260,855

[22] Filed: Oct. 21, 1988

[51] Int. Cl.[5] ............................................ C07C 311/41
[52] U.S. Cl. ...................................................... 564/82
[58] Field of Search ........................ 564/82, 83, 82.1; 514/603

[56] References Cited

U.S. PATENT DOCUMENTS 4,544,654 10/1985 Davey et al. .................... 514/210
4,721,809 1/1988 Buzby et al. ...................... 564/82

Primary Examiner—Richard L. Raymond
Attorney, Agent, or Firm—Richard K. Jackson

[57] ABSTRACT

This invention provides Class III anti-arrhythmic agents of the formula:

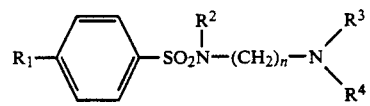

in which $R^1$ is alkylsulfonamido, $R^2$ is ethyl, $R^3$ is hydrogen, $R^4$ is ethyl, and n is 2 to 4, or a pharmaceutically acceptable salt thereof.

3 Claims, No Drawings

ANTI-ARRHYTHMIC AGENTS

RELATED DISCLOSURES

U.S. Pat. No. 4,721,809 granted Jan. 29, 1988 to George C. Buzby, Jr. and Thomas J. Colatsky currently subject to reexamination discloses and claims a family of secondary and tertiary substituted sulfonamides as Class III antiarrhythmic agents.

BACKGROUND OF THE INVENTION

Class III anti-arrhythmic agents may be categorized as having the ability to markedly prolong dog Purkinje fiber action potential duration without producing significant changes in maximal upstroke velocity. Unlike Class I anti-arrhythmic agents, a pure Class III agent displays no effects on cardiac sodium channels. The electrophysiologic properties of a compound defining a Class III activity profile are observed in vivo as negligible effects on atrial, ventricular and H-V conduction times while producing a marked increase (greater than 20 percent) in both the atrial and ventricular refractory period. In contrast, Class I agents will demonstrate a marked slowing of ventricular conduction velocity, generally without significant changes in the refractory period. Recent reviews of these agents are by Bexton et al., Pharmac. Ther. 17, 315-55 (1982); Vaughan-Williams, J. Clin. Pharmacol. 24, 129-47 (1984) and Thomis et al., Ann. Rep. Med. Chem. 18, 99-108 (1983).

German Offenlegungsschrift 1912848 discloses in Example 5 the intermediate $N^1$-(2-isopropylaminoethyl)-$N^4$-acetyl-sulfanilamide which is used to produce 1-sulfanilyl-2-imino-3-isopropyl-imidazolidin said to be useful as a hypoglycemic agent.

Silberg et al., ACAD Rep. Populace Romire, Fillala Clug, Studee Cercetari Med., 10 244-52 (1959) discloses p-acetylamino-N-(2-diethylaminoethyl)benzenesulfonamide among other compounds compared in their anti-arrhythmic properties with procainamide.

The Abstracts of Papers to be presented at the 192nd ACS National Meeting, Sep. 7-12, 1986 at Anaheim, Calif. reports Abstract 9 by R. A. Wohl et al. which discloses N-[2-(diethylamino)ethyl]-4-[(methylsulfonyl)amino] benzamide hydrochloride projected as a potential Class III anti-arrhythmic agent.

The Abstracts of Papers to be presented at the 192nd ACS National Meeting, Sep. 7-12, 1986 at Anaheim, Calif. reports Abstract 9 by R. A. Wohl et al. which discloses N-[2-(diethylamino)ethyl]-4-[(methylsulfonyl)amino] benzamide hydrochloride projected as a potential Class III anti-arrhythmic agent.

U.S. Pat. No. 4,544,654 granted Oct. 1, 1985 claims the specific carbonamide named in the preceding paragraph and names the correspondingly substituted sulfonamide species as well as disclosing a genus of sulfonamides corresponding in structure to the generically claimed carbonamides. All the tertiary amines disclosed are said to be Class III antiarrhythmic agents.

EP 0 158 775 published Oct. 23, 1985 presents essentially the same tertiary amine disclosure as the preceding U.S. patent and in addition discloses a genus of secondary amines in which the terminal N-substituted may be an alkyl group containing from 5 to 10 carbon atoms. Secondary amines with less than five carbon alkyl substitution were excluded as inactive Class III antiarrhythmic agents.

U.S. Pat. No. 4,629,739 granted Dec. 16, 1986 claims the secondary amine containing carbonamide derivatives common with EP 0 158 775 and discloses a sulfonamide genus of comparable scope with the claimed carbonamide genus. An N-heptyl substituted sulfonamide compound species is disclosed.

DESCRIPTION OF THE INVENTION

In accordance with this invention there is provided a group of anti-arrhythmic agents classified by their pharmacological profile as Class III anti-arrhythmic agents of the formula:

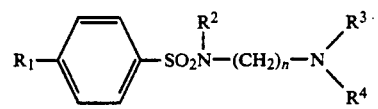

in which
$R^1$ is alkylsulfonamido of 1 to 6 carbon atoms;
$R^2$ is ethyl;
$R^3$ is hydrogen;
$R^4$ is ethyl; and
n is one of the integers 2, 3 or 4;
or a pharmaceutically acceptable salt thereof.

Preferred compounds of the group described above are those in which $R^1$ is $CH_3SO_2NH-$. The most preferred compound is:

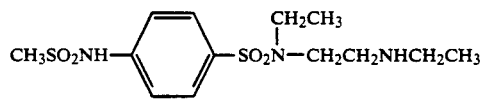

or a pharmaceutically acceptable salt thereof.

The pharmaceutically acceptable salts of the anti-arrhythmic agents of this invention are prepared directly by neutralization of the free base. These physiologically acceptable salts may be formed with organic or inorganic acids such as hydrochloric, hydrobromic, phosphoric, sulfuric, sulfamic, nitric, methysulfonic, acetic, maleic, succinic, fumaric, tartaric, citric, salicylic, lactic, naphthalenesulfonic acid, and the like.

The compounds of this invention may be prepared by reaction of an appropriately substituted benzene sulfonyl halide with an appropriately substituted $\alpha,\omega$-alkane diamine of 2 to 4 carbon atoms. These reactants are generally known compounds and otherwise are routinely prepared by techniques well within the skill of the chemist. The compounds may also be prepared by acylation of a free amino group on the benzene ring of the desired sulfonamide in the absence of an $\omega$-nitrogen proton, as with trifluoromethylsulfonylanhydride and the like, in the presence of an acid binding agent such as triethylamine.

The compounds of this invention demonstrate anti-arrhythmic activity when tested in the standard experimental animal in accordance with the following procedure:

Miniature pigs of either sex weighing 11-24 kg were anesthetized by administration of 35 mg/kg sodium pentobarbital i.p. and ventilated with room air following tracheotomy using a Harvard respirator pump set to deliver 20 ml/kg at a rate of 20/min. The left femoral artery and vein were cannulated for the recording of blood pressure and for drug administration, respectively. Blood pressure and lead II EKG were recorded on a Beckman RM dynograph recorder (Model R-612).

The heart was exposed by a left thoracotomy performed at the fifth intercostal space. A silk ligature was placed beneath the left anterior descending coronary artery (LAD) about 1 cm from its origin and distal to the septal artery branch. The artery was occluded by lifting the vessel with the ligature and quickly placing a bull-dog clamp (3×12 mm pudded jaws) over the artery. The clamp remained in place for a period of 20 min. Removal of the clamp produced a rapid reperfusion of the ischemic myocardium as evidenced by the return of normal color to the myocardium distal to the site of occlusion. Ectopic activity was monitored during occlusion and reperfusion by recording the lead II EKG at chart speeds of 5-25 mm/s. Animals were allowed to stabilize for at least 30 min prior to drug administration.

Pigs were randomized into groups receiving either vehicle or test drug at 5 mg/kg i.v. Animals surviving the period of occlusion were subsequently reperfused. No attempt was made to resuscitate animals experiencing ventricular fibrillation (VF) at any time following occlusion. Efficacy was established by noting the rate of survival of treatment vs. control groups using Fisher's exact test or Mantel-Haenszel test for the survival curves. In the absence of treatment, less than 30 percent of the animals survive the period of occlusion, with a mean time to death onset of 8-12 min. An effective compound either prevented death or prolonged survival time.

The compounds of this invention display a Class III anti-arrhythmic profile. Of these, the products of Examples 1 and 4 are representative. The Class III antiarrhythmic activity was established in accordance with the following standard test procedure:

Bundles of free-running Purkinje fibers with attached myocardium obtained from either ventricle of adult dog heart were pinned without stretching to the bottom of a 10 ml tissue chamber and continuously superfused with oxygenated Tyrode's solution at a flow rate of 10 ml/min. The composition of the Tyrode's solution was (mM): NaCl 150; KCl 4.0; $CaCl_2$ 2.7; $MgCl_2$ 0.5; HEPE buffer (7.4) 10; dextrose 5.5. The solution was aerated with 100% $O_2$. Bath temperature was maintained at 36±0.5° C. by circulating the superfusate through a thermostatically controlled water bath immediately prior to entering the tissue chamber.

The preparations were stimulated through bipolar Telfon-coated platinum wires, bared at the tips, placed on the endocardial surface of the attached myocardium, using a W.P.I. digital stimulator set to deliver constant current pulses 1-2 msec in duration at cycle lengths (c.l.) of 330 or 1000 msec. Stimulus strength was set at approximately 2× diastolic threshold, and adjusted as required throughout the experiment. All preparations were allowed to equilibrate in the tissue chamber for at least 1 hour before measurements were begun. Subsequently, a minimum of 60 minutes was allowed for equilibration with each drug-containing superfusate before post-drug measurements were made. Impalements were made at 6-10 sites throughout the preparation before and after drug exposure. Offset potentials were re-checked at the conclusion of each experiment.

Glass microelectrodes filled with 3M KCl were coupled to high impedance negative capacitance electrometers (W. P. Instruments, New Haven, Conn.), and Ag/AgCl half-cells used as reference electrodes. The first derivative of the action potential upstroke (Vmax) was obtained using an analog differentiator circuit, coupled to a peak-hold circuit that retained the recorded value of Vmax for 30-70 msec. Action potential and Vmax tracings were displayed on a Tektronix storage oscilloscope, and photographed for later analysis. In addition, chart paper recordings of Vmax were obtained using the peak-hold device output.

Fresh stock solutions of drug were prepared for each experiment. Compounds were dissolved in distilled water at total concentrations of 1-10 mg/ml, and subsequently diluted to a final concentration of 3 μM in appropriate volumes of normal Tyrode's solution for evaluation.

Action potential (AP) parameters measured included: diastolic take-off potential (or activation voltage, $V_{act}$); AP overshoot ($V_{os}$); AP duration measured as the time taken to repolarize to −20 mV ($APD_{20}$), −60 mV ($APD_{60}$), and −80 mV ($APD_{80}$); and maximal upstroke velocity (Vmax). Data were compared using a two-sample t-test, with statistical significance taken as $p<0.05$. An increase in $APD_{60}$ that occurred without a significant change in Vmax was taken, by definition, to indicate Class III anti-arrhythmic activity.

Based upon the activity profile elicited by the compounds of this invention in the above-described standard scientifically recognized test models, the compounds are established as anti-arrhythmic agents useful in the treatment of cardiac arrhythmias and conditions characterized by coronary arteries vasospasm. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from about 1 to about 5 milligrams per kilogram host body weight (preferably from 2 to 10 mg/kg) i.v., and from about 2 to about 10 mg/kg (preferably 5 to 20 mg/kg) p.o., to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 50 milligrams to about 400 milligrams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following example illustrates the preparation of a compound of this invention. After the example, the change in action potential duration and upstroke velocity are provided.

EXAMPLE

4-Methylsulfonamido-N-(ethyl)-N'-[2-[(ethyl)-amino]ethyl]benzenesulfonamide

4-Methylsulfonylaminobenzenesulfonyl chloride (9.3 g, 0.0345 mol) was added as a solid (portion-wise) to a solution of N,N'-diethylethylenediamine (8.0 g, 0.069 mol) in methylenechloride (300 ml) at 0° C. while stirring. The formed precipitate was separated by filtration and discarded. The filtrate was taken to dryness and the residue was chromatographed (HPLC) through a Waters Prep. Pak ®-500/silica gel column using methanol 5 to 40% gradient with ethyl acetate. The fractions were separated to give the product as an oily residue after solvent removal. The title compound (5.3 g) solidified upon standing. It was recrystallized from methanol to give 3.5 g of pure product, m.p. 169°–170° C.

Elemental Analysis for: $C_{13}H_{23}N_3O_4S_2$; Calc'd: C, 44.68; H, 6.63; N, 12.02. Found: C, 44.69; H, 6.55; N, 12.06.

3 μm, 1000 msec c.l. (free base in aqueous HCl solution): % $\Delta APD_{60} = 36 \pm 5.8$; % $\Delta V_{max} = 2 \pm 3.5$

What is claimed is:

1. A compound of the formula:

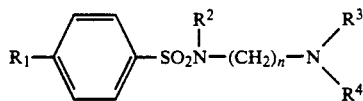

in which
 $R^1$ is alkylsulfonamido of 1 to 6 carbon atoms;
 $R^2$ is ethyl;
 $R^3$ is hydrogen;
 $R^4$ is ethyl; and
 n is one of the integers 2, 3 or 4; or a pharmaceutically acceptable salt thereof.

2. A compound of claim 1 in which $R^1$ is $CH_3SO_2NH$; or a pharmaceutically acceptable salt thereof.

3. A compound of claim 1 which is 4-methylsulfonamido-N-(ethyl)-N'-[2-[(ethyl)amino]ethyl]benzenesulfonamide.

* * * * *